United States Patent [19]

Effron et al.

[11] Patent Number: 4,601,290
[45] Date of Patent: Jul. 22, 1986

[54] SURGICAL INSTRUMENT FOR CUTTING BODY TISSUE FROM A BODY AREA HAVING A RESTRICTED SPACE

[75] Inventors: Marc H. Effron, New Hope; Henry J. Tancredi, Gwynedd, both of Pa.

[73] Assignee: Cabot Medical Corporation, Langhorne, Pa.

[21] Appl. No.: 540,319

[22] Filed: Oct. 11, 1983

[51] Int. Cl.⁴ ............................................. A61F 17/32
[52] U.S. Cl. .................................................. 128/305
[58] Field of Search ............... 128/305, 751, 752, 755; 74/104, 107, 99 A

[56] References Cited

U.S. PATENT DOCUMENTS

| | | | |
|---|---|---|---|
| 3,732,858 | 5/1973 | Banko | 128/753 |
| 3,776,106 | 12/1973 | Pish | 74/99 A |
| 4,203,444 | 5/1980 | Bonnell et al. | 128/305 |
| 4,274,414 | 6/1981 | Johnson et al. | 128/305 |
| 4,306,570 | 12/1981 | Matthews | 128/755 |
| 4,316,465 | 2/1982 | Dotson, Jr. | 128/305 |

OTHER PUBLICATIONS

Trylon, Diamond-Edges Scissors,-Trylon Surgical Instruments Catalogue, (Aloe Medical 1971).

Primary Examiner—C. Fred Rosenbaum
Assistant Examiner—Mario Costantino
Attorney, Agent, or Firm—Austin R. Miller

[57] ABSTRACT

A surgical instrument and method for cutting and removing body tissue from a body area having a restricted space is provided. The cutter comprises an external cutting tube sized for insertion into the restricted space. The external tube has an opening therein with cutting edges thereon. An internal tube having an internal opening therein with cutting edges thereon is positioned within the external tube. The openings in the external and internal tubes are relatively oscillatingly movable to open to receive body tissue therethrough and to close to cut the body tissue. A vacuum is provided to draw the cut body tissue into and through the internal tube and out of the instrument.

13 Claims, 10 Drawing Figures

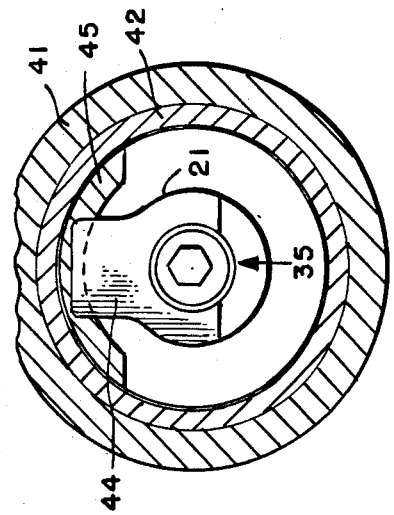
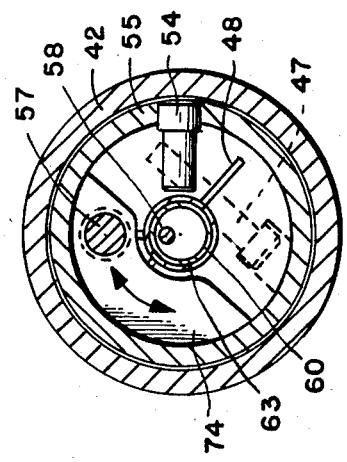
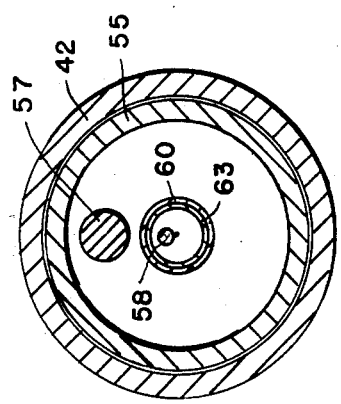
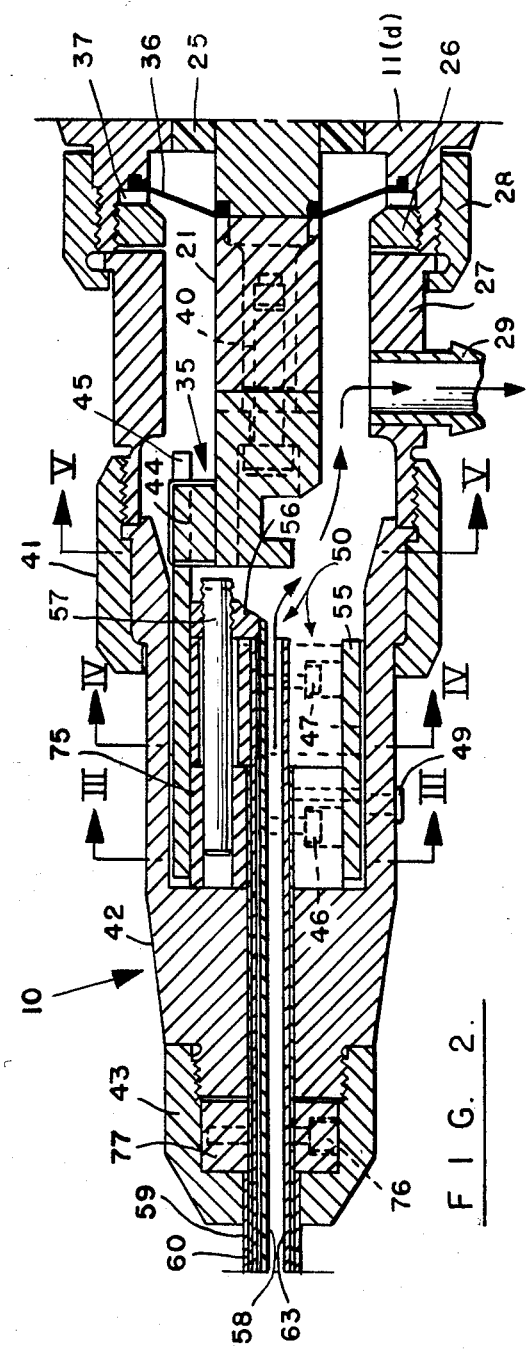

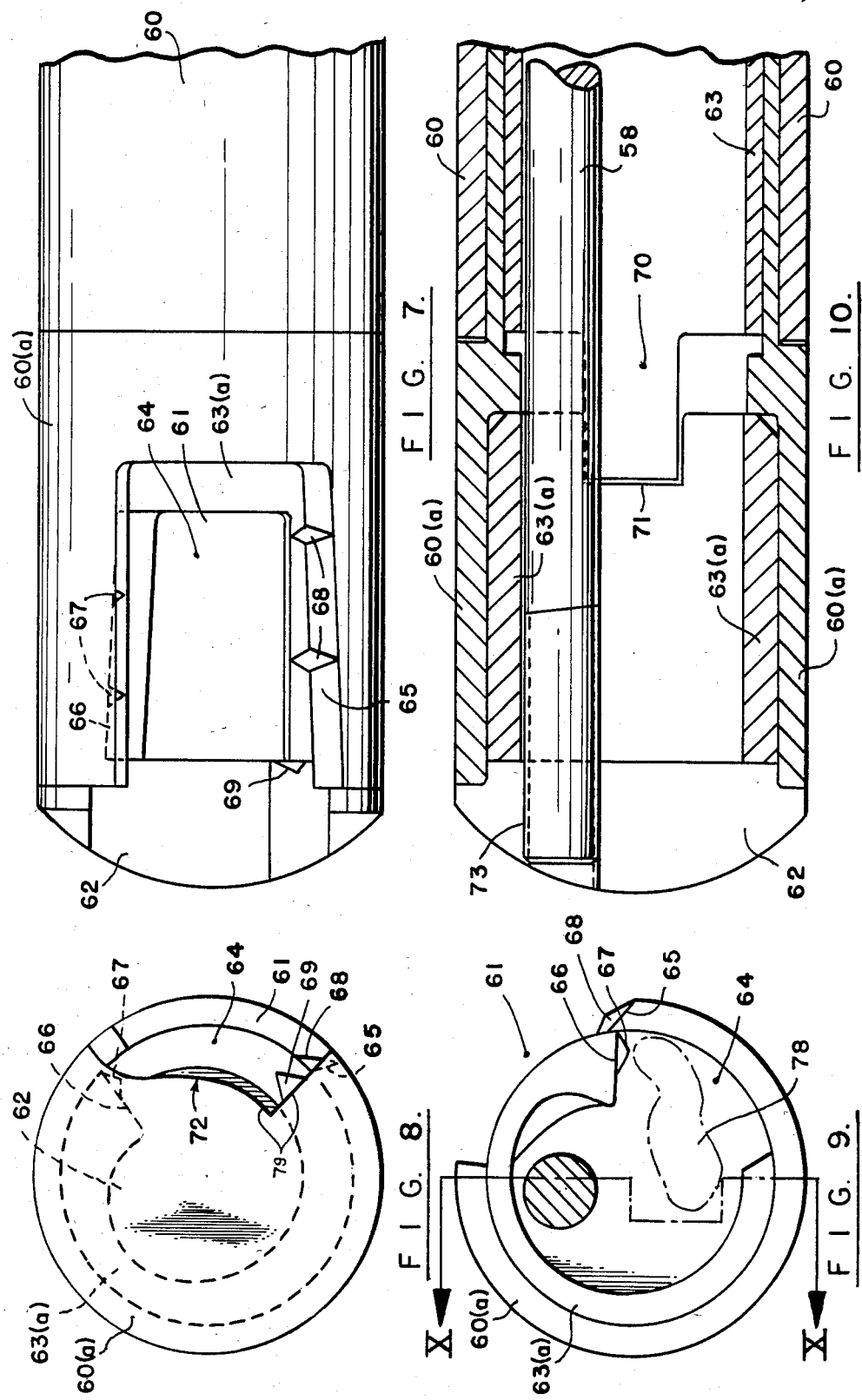

SURGICAL INSTRUMENT FOR CUTTING BODY TISSUE FROM A BODY AREA HAVING A RESTRICTED SPACE

BACKGROUND OF THE INVENTION

1. Field of the Invention

The present invention relates to a surgical instrument for cutting and removing body tissue from a body area having a restricted space, and more specifically relates to such an instrument capable of performing joint surgery in body joints such as the knee utilizing surgical viewing probes inserted through punctures into the joint regions, without laying open the joint.

2. Description of the Prior Art

In body joints such as the knee having severely restricted operating space, it is impractical to use a cutter having jaws which must expand in order to open and cut since in many instances the restricted space is insufficient to allow the cutting jaws to open. In response to this limitation, a number of surgical instruments have been developed utilizing cutters which do not open and expand to cut body tissue. U.S. Pat. No. 4,203,444 to Bonnell et al discloses such a cutter. The Bonnell device utilizes an outer tube having a side-facing, axially extending cutting port and an internal rotary blade. A vacuum conduit draws the body tissue to be shaved into the cutting port while the rotary blade is driven in shearing relation to the external tube. The vacuum further draws the cut body tissue through the inner tube and out of the instrument for disposal.

One serious problem encountered with the Bonnell device is in cutting thin, soft fibrous material as is typically found in the knee joint. The rotating blade of the Bonnell device has a tendency to pull and spool such soft fibrous materials. Eventually, such spooling can bind the rotating cutting blade and also clog the aspiration chamber.

A further disadvantage of the Bonnell device is encountered after repeated use of the instrument on dense tough body tissues such as the meniscus tissue in the knee joint. After prolonged use, the rotary cutting blades of the Bonnell device become dulled and the meniscus tissue simply pops out of the cutting port as the rotating cutter blades spin resulting in little or no cutting of the meniscus tissue.

OBJECTS OF THE INVENTION

It is an important object of the present invention to provide a surgical cutting device for cutting and removing body tissue from a body area having restricted space wherein the space taken up by the cutter during the opening and closing of the cutting edges remains constant.

It is another important object of the present invention to provide such a surgical cutting instrument having good durability and cutting edges which do not become easily dulled.

Another important object of the present invention is to provide such a surgical cutting instrument having no tendency to become spooled and clogged when the surgeon is cutting thin soft fibrous material.

It is another important object of the present invention to provide a cutting instrument able to easily cut the tough dense body tissue such as the meniscus of the knee without the body tissue slipping out of the cutting jaws.

It is a further important object of the present invention to provide a surgical cutting instrument having cutting tips which connect and disconnect quickly and easily allowing the surgeon to change cutting tips rapidly during an actual operation.

It is a further important object of the present invention to provide such a surgical cutting instrument which is entirely steam autoclavable.

It is yet another important object of the present invention to provide a tissue collection system with the surgical cutting instrument allowing the surgeon to view the tissue which has already been cut.

SUMMARY OF THE INVENTION

A surgical instrument for cutting and removing body tissue from a body area having restricted space in accordance with this invention includes an external tube sized for insertion into the restricted space and having an external opening therein having cutting edges thereon. An internal tube is positioned within the external tube and has an internal opening therein having cutting edges thereon. The external and internal openings and cutting edges are relatively moveable to open to receive the body tissue therethrough and to close in order to cut the body tissue. A vacuum producing means, operative to draw a vacuum within the internal tube, is provided in order to draw the body tissue in through the external and internal openings. A cutter driver means oscillatingly displaces the internal tube and the external tube with respect to one another causing the internal and external cutting edges to cut the body tissue, whereby the vacuum producing means draws the cut body tissue away from the internal and external openings and removes the body tissue after it is cut.

A method for surgically cutting and removing body tissue from an area having restricted space in accordance with this invention includes placing the cutter adjacent the body tissue so that the body tissue is immediately adjacent the external openings in the tubes. The external and internal openings having cutting edges are opened and the body tissue is drawn into the openings. The external and internal tubes are oscillatingly displaced with respect to one another causing the internal and external cutting edges to cut the body tissue. The cut body tissue is then drawn away from the openings, through the instrument and removed.

BRIEF DESCRIPTION OF THE DRAWINGS

FIG. 2 is a sectional view of a middle portion of an instrument according to another embodiment of the present invention.

FIG. 3 is a sectional view taken along line III—III in FIG. 2.

FIG. 4 is a sectional view taken along line IV—IV in FIG. 2.

FIG. 5 is a sectional view taken along line V—V in FIG. 2.

FIG. 7 is a side view of the forward tip of an apparatus according to one embodiment of the present invention showing the internal and external openings and cutting edges in the open position.

FIG. 8 is an end view of the forward tip of the apparatus shown in FIG. 7.

FIG. 9 is a sectional end view of the forward tip of an instrument showing the internal and external openings and cutting edges in the closed position.

FIG. 10 is a side view, shown in section, taken along the line X—X in FIG. 9.

Figure 1:
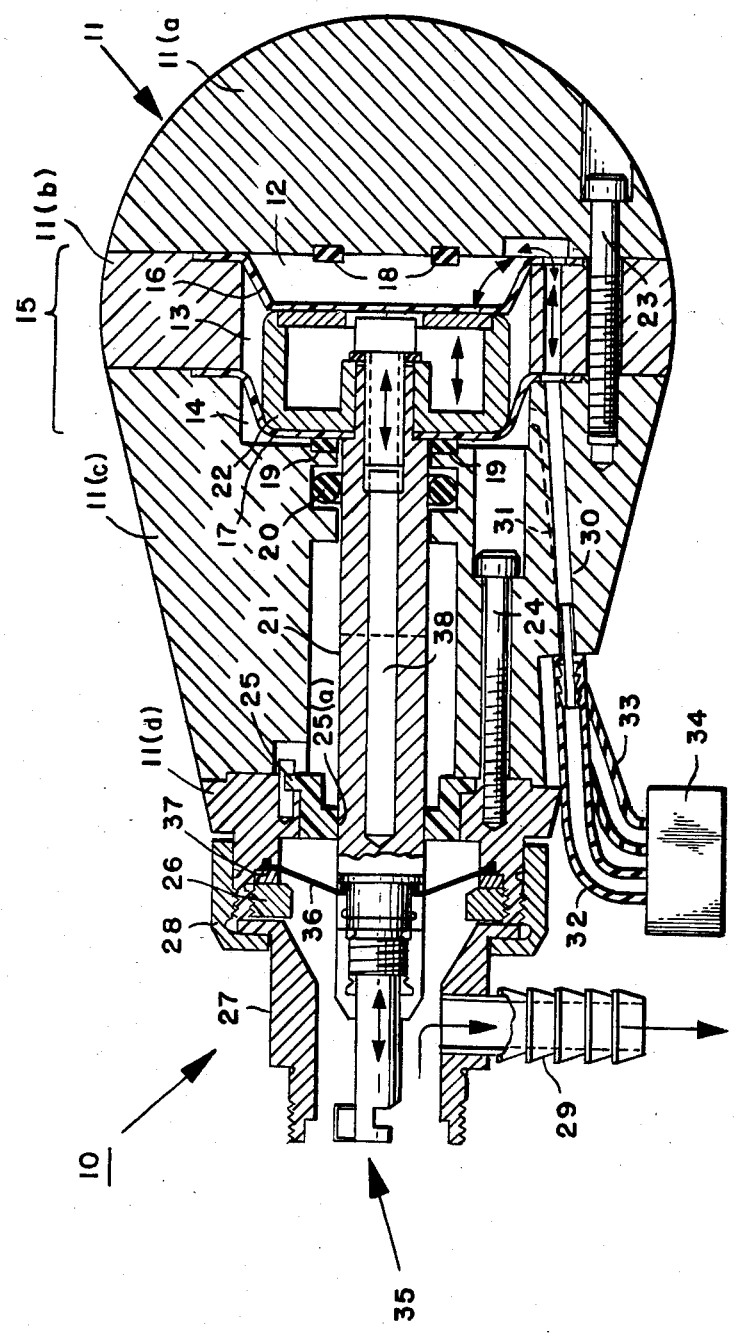
FIG. 1 is a sectional view of a rearward portion of an instrument according to one embodiment of the present invention.

Although specific forms of apparatus embodying the invention have been selected for illustration in the drawings, and although specific terminology will be resorted to in describing those forms and the method steps which the apparatus performs in the specification which follows, their use is not intended to define or to limit the scope of the invention, which is defined in the appended claims.

DESCRIPTION OF THE PREFERRED EMBODIMENTS

Referring to the drawings, the surgical cutter of the present invention is designated as 10. Furthermore, with respect to the cutter 10 and/or any individual part thereof, the side or end closest to the patient shall be designated forward and the side or end closest to the surgeon shall be designated rearward.

In the Figures, the same or similar parts are labelled with the same number.

Referring to FIG. 1, the rearward end of the surgical cutter 10 is shown. The handle 11 of the surgical cutter 10 comprises a rounded rear handle 11(a) constructed of solid aluminum and shaped to comfortably fit within the palm of the surgeon's hand. Rear handle 11(a) is fixedly attached to middle handle 11(b) by a plurality of bolts 23.

Likewise, forward handle 11(c) is fixedly attached to the forward side of middle handle 11(b) by bolts 23. Fixedly attached to the forward face of forward handle 11(c) is forwardmost handle 11(d), attached by bolts 24. As is shown in FIG. 1, handles 11(b), 11(c) and 11(d) are annularly shaped. Within handles 11(b) and 11(c) is a chamber 15. Chamber 15 is divided by diaphragms 16, 17 into a forward chamber 14, a middle chamber 13 and a rearward chamber 12.

Positioned within handle 11(c) is piston 21 having at its rearward end an enlarged piston head 22. Piston head 22 is positioned between the flexible diaphragms 16, 17 and is fixedly attached to diaphragm 17.

Fluidly connected to rearward chamber 12 is a passageway 30. Fluidly connected to forward chamber 14 is a passageway 31. Passageways 30 and 31 are connected in fluid sealing relation to tubes 32, 33, respectively. Tubes 32, 33 connect with nitrogen supply system 34. In a known manner, nitrogen is alternately supplied at a positive pressure to each of the tubes 32, 33 thereby alternately causing the rearward chamber 12 and the forward chamber 14 to become pressurized. Such alternating pressurization causes the diaphragms 16, 17 to flex thereby giving the piston head 22 and piston 21 an alternating forward and rearward motion, as shown by the arrows in FIG. 1.

Rubber bumpers 18 and 19 are provided to cushion the impact of the piston head 22 against handles 11(a) and 11(c). This cushioning helps to eliminate inertial movement of the cutter 10 during use.

Nitrogen supply system 34 alternately feeds tubes 32 and 33 with nitrogen under constant pressure. In this way, a constant force is applied to the piston head 22 in both the forward and rearward strokes. Furthermore, nitrogen supply system 34 contains appropriate control means allowing the surgeon to vary the frequency with which nitrogen is alternately pumped to the tubes 32, 33. The control means also allows the surgeon to vary the dwell time of the piston 21 in either the forwardmost or rearwardmost position.

An O-ring is provided at the forward side of diaphragm 17 surrounding piston 21. O-ring 20 prevents nitrogen leakage into the portion of the instrument forward the O-ring 20.

Sealingly positioned between piston 21 and handle 11(d) is an annular anti-blow back seal 36. Seal 36 is typically constructed of silicone. The outer edge of seal 36 is secured to handle 11(d) by gasket 37 and threaded ring 26.

Piston 21 is positioned in sliding relation to piston support 25. Piston support 25 has a square shaped interior opening 25(a). Furthermore, piston 21 has a square cross sectional shape in the area adjacent piston support 25. This construction prevents rotation of piston 21 during operation of the instrument.

Piston 21 has an interior space 38 which effectively lowers the mass of the oscillating piston 21 helping to prevent inertial movement of the cutter 10 during use.

Ring 28 threadably engages handle 11(d) thereby clamping and fixedly securing flanged member 27 to handle 11(d). Member 27 has a side extending aspirator tube 29. Attached to the forward end of piston 21 is a quick disconnect member 35 whose operation will be described in more detail hereinafter.

Referring now to FIG. 2, a middle portion of a surgical cutter 10, similar to the surgical cutter 10 illustrated in FIG. 1, is shown. As in the cutter shown in FIG. 1, the middle portion of cutter 10 connects with the forward end of handle 11(d) and the forward end of piston 21.

Ring 28 threadably attaches to handle 11(d) and clamps flanged member 27 in place at the forward end of handle 11(d). Washer 37 and threaded ring 26 are seated within the forward end of handle 11(d) and hold diaphragm 36 in place. Flanged member 27 has a side extending aspirator tube 29. A vacuum tube can be connected to the aspirator tube 29 in a known manner to provide suction to the interior of cutter 10. Adjacent the forward end of flanged member 27 is body member 42, secured in place by ring 41. Threaded onto the forward end of body member 42 is cannula 43 having a cannula sleeve 59. The cannula sleeve 59 is shown in the withdrawn position. With the use of the cutter 10 the surgeon typically makes an initial shallow incision in the muscle and fatty tissue of the body area undergoing operation. Next, the forward end of the cannula sleeve 59 is inserted into the incision. The surgeon then typically uses a trocar, inserted through the cannula sleeve 59, to provide an opening to the internal body area to be operated on. The trocar is then withdrawn from the cannula 43 and the cutter 10 is inserted into the cannula 43. After insertion of the cutter 10, the cannula 43 is withdrawn and fastened in place at the forward end of body member 42 substantially as shown in FIG. 2. When the surgeon is ready to withdraw the cutter 10, the cannula 43 is unscrewed from body member 42, advanced into the surgical wound and the cutter 10 is slid rearwardly out of cannula tube 59. In this way, the cutting tip of the cutter 10 avoids snagging and pulling the soft fatty and muscle tissues surrounding the wound.

Positioned within body member 42 is barrel-cam member 50 having a rearwardly extending arm 45 which releasably connects with member 44. Member 44 is typically part of a quick-disconnect means 35 allowing the surgeon to quickly and easily change the forward portions of the cutter during operating procedures.

As shown in FIGS. 1 and 2, the piston 21 is in its forwardmost position. Hence, barrel-cam member 50 is also in its forwardmost position. Thus, as piston 21 oscillates forwardly and rearwardly, so does barrel 55 of barrel-cam member 50.

Figure 6:
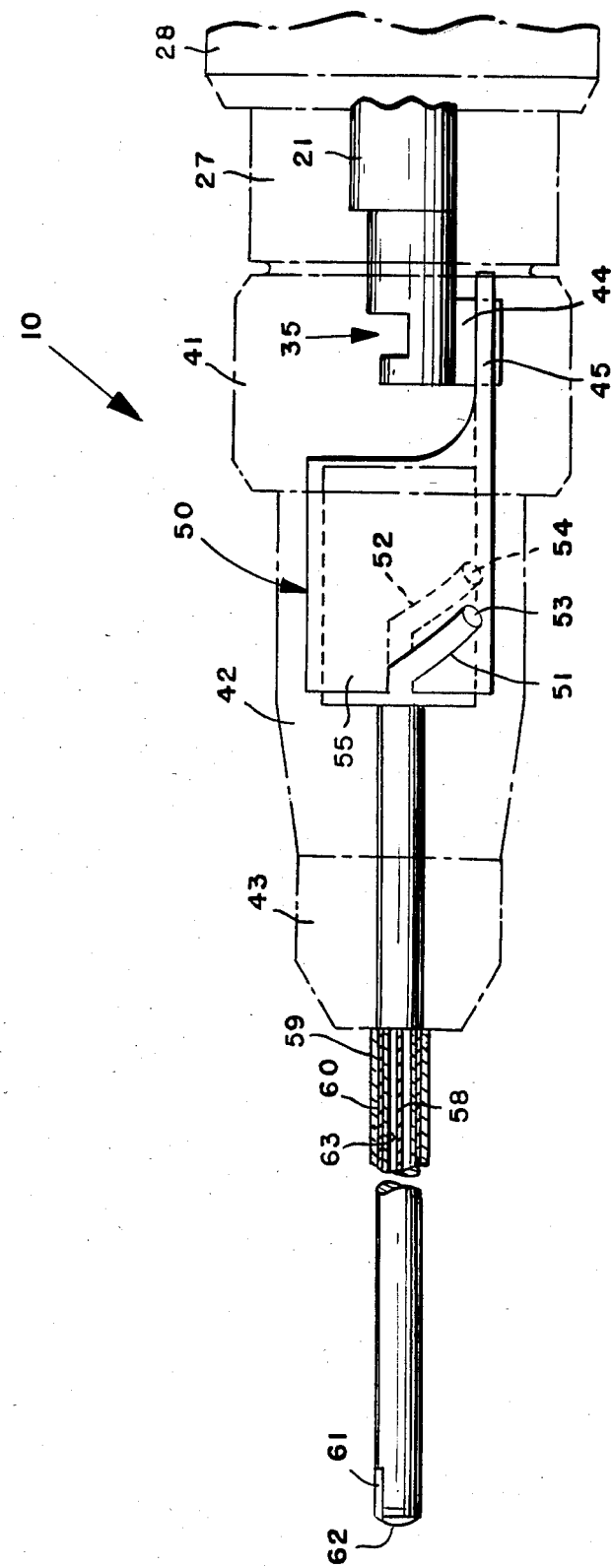
FIG. 6 is a side view, shown partly in section, of the middle and forward portions of an instrument according to one embodiment of the present invention, specifically illustrating the barrel cam means of the apparatus.

As is clearly shown in FIG. 6, barrel 55 has slots 51, 52 therein. Further, cam following pins 53, 54 ride within slots 51, 52 respectively. Cam following pins 53, 54 are connected to tubes 60, 63 and cause the tubes 60, 63 to oscillatingly rotate in opposite directions as the piston 21 and barrel-cam member 50 oscillate forwardly and rearwardly.

As shown in FIG. 4, cam following pin 54 is fixedly secured to inner tube 63 by split ring 48 and tube clamping screw 47. Thus, as barrel cam member 50 oscillates in a forward-rearward manner, cam following pins 53, 54 move in slots 51, 52, respectively, causing the inner tube 63 and the outer tube 60 to rotate in opposition directions in an oscillating manner. As shown in FIG. 2, a tie rod 58 is positioned within inner tube 63. The rearward end of tie rod 58 is secured in jacking block 56. Jacking block 56 threadably engages jacking screw 57 which is secured in member 75. As shown in FIG. 10, the forward end of tie rod 58 is threadably secured to the front cutter 62 by engagement with threaded opening 73. Thus, as jacking screw 57 is screwed into jacking block 56, a tension is exerted on tie rod 58.

Thus, as inner tube 63 rotates, so do member 75, jacking screw 57, jacking block 56 and tie rod 58. As shown in FIG. 4, jacking screw 57 travels within slot 74 so as not to interfere with the rotation of the outer tube in the opposite direction.

Similar to tube clamping pins 46, 47, pin 76 positioned within member 77 helps secure outer tube 60. Thus, as outer tube 60 oscillatingly rotates, so does pin 76 and member 77.

Turning now to FIGS. 7-10, there are shown various views of the forward end of cutter 10. As shown in FIG. 10, internal tube 63 is keyed to internal cutting tube 63(a) by key 70 positioned within key way 71. In a similar manner, external cutting tube 60(a) is keyed to external tube 60. Cutting tubes 60(a) and 63(a) are preferably constructed of carbide, providing better cutting and extended wear characteristics.

Positioned at the forward end of cutting tubes 60(a) and 63(a) is forward cutter 62 having threaded opening 73 therein. As was described earlier, cutter 62 rotates with external tube 60 and external cutting tube 60(a) and tie rod 58. Thus, tie rod 58 oscillates along a curved pathway as the external tube 60, the external cutting tube 60(a) and the front cutter 62 oscillatingly rotate.

Referring to FIG. 7, there is shown an exterior side view of the forward end of the cutter 10. External cutting tube 60(a) has an opening 61 therein having a cutting edge 65 with gripping teeth 68 positioned thereon. Similarly, inner cutting tube 63(a) has an opening 64 therein having a cutting edge 66 with gripping teeth 67 positioned thereon. As the cutting tubes 60(a) and 63(a) oscillatingly rotate, the openings 61, 64 alternate between a position of registry, wherein the cutting edges 65, 66 are open, and a position of non-registry wherein the cutting edges 65, 66 are closed. As the cutting tubes 60(a) and 63(a) oscillatingly rotate, the edges 65, 66 alternately open and close.

The end view of the forward tip of cutter 10 is shown in FIG. 8. An opening in the forward end of the front cutter 62 is defined by front opening 72 having front cutting edge 79. When the cutting jaws are open, the internal opening 64 and the external opening 61 are in registry with the opening defined by the cutting edge 79. In this way, the surgeon can cut tissue immediately forward the tip of the cutter 10 as well as material at the side of the openings 64, 61. In this way, the surgeon can "scoop" body tissue into the cutting jaws by moving the cutter 10 forwardly or rearwardly. Front cutter 62 has a tooth 69 which helps hold this scooped tissue in place as the cutting edges 65, 66 close. As is shown in FIG. 8, internal cutting tube 63(a) is enlarged in the region of cutting edge 66 to ensure that the forward opening defined by edge 79 is completely closed off when the cutting edges 65, 66 are in a closed position.

Referring to FIG. 9, there is shown a sectional view of the cutting tubes 60(a) and 63(a) in the closed position immediately after cutting body tissue 78.

In the operation of the cutter 10, a vacuum is continually applied through aspirator tube 29 which produces a vacuum within the interior of internal tube 63 and internal cutting tube 63(a). Thus, as body tissue 78 is cut, it is sucked rearwardly through the interior of internal cutting tube 63(a) and internal tube 63 and out of the instrument through aspirator tube 29 as shown by the arrows in FIG. 2.

As previously mentioned, the pneumatic logic used in conjunction with cutter 10 allows the surgeon to control the frequency with which the cutting edges 65, 66 open and close as well as the dwell time of the cutting edges 65, 66 in the open and closed positions. However, the speed (and timing) of the cutting edges 65, 66 during opening and closing remains constant. This means that the cutting force of the edges 65, 66 also remains constant.

It should be understood by those skilled in the art that many other cutting tip configurations may be used with the cutter 10 of the present invention. For example, another cutting tip configuration utilizes a stationary (i.e. non-rotating, non-oscillating) external cutting tube having an open forward tip and an oscillating but non-rotating internal cutting tube having a side facing opening therein. As the internal tube with the side facing opening extends out of the tip of the external cutting tube, body tissue is sucked into the side facing opening and is sheared off as the internal cutting tube is drawn back into the external cutting tube. This type of device utilizes no barrel cam member since the internal tube merely oscillates in a forward-rearward direction and does not rotate.

By the term "oscillating" or "oscillatingly" when describing the relative motions of the internal and external tubes, I intend to encompass the following situations: (1) a stationary (i.e. non-rotating, non-oscillating) external tube and an internal tube moving in an oscillating forward-rearward manner; (2) a stationary internal tube and an external tube moving in an oscillating forward-rearward manner; (3) both the internal and external tubes moving in oscillating forward-rearward manners, the direction of movement of the tubes being in opposite directions at any one time; (4) a stationary outer tube and an internal tube moving in an oscillating rotational (i.e. clockwise-counterclockwise) manner; (5) a stationary internal tube and an external tube moving in an oscillating rotational manner; (6) both the internal and the external tubes moving in oscillating rotational manners, the internal and external tubes moving in the opposite rotational direction at any one time; and (7) any combination of the above movements (1)–(6).

Although this invention has been described in connection with specific forms thereof, it will be appreciated by those skilled in the art that a wide variety of equivalents may be substituted for those specific elements and steps of operation shown and described herein, that certain features may be used independently of other features, and that parts may be reversed, all without departing from the spirit and scope of this invention as defined in the appended claims.

We claim:

1. In a surgical instrument for cutting and removing body tissue from a body joint having a restricted space, a cutter comprising a body member and:
   (a) an elongated external tube carried by the body member and sized for insertion into the restricted space and having an external opening therein extending longitudinally of said tube and having a cutting edge thereon;
   (b) an internal tube also carried by the body member and positioned within the external tube and having an internal opening therein extending longitudinally of said internal tube and having a cutting edge thereon;
   (c) the external and internal openings and cutting edges each being relatively movable with respect to the body member and movable concurrently in opposite directions with respect to the longitudinal axes of the tubes to open to receive the body tissue therethrough and to close to cut the body tissue;
   (d) vacuum means operative to draw a vacuum within the internal tube, for drawing the body tissue in through the external and internal openings;
   (e) cutter drive means operative to oscillatingly drive the internal tube and the external tube relative to said body member and in opposite rotational directions causing the internal and external cutting edges to cut the body tissue, whereby the vacuum means draws the cut body tissue away from the internal and external openings; and
   (f) cutter drive control means for independently varying (i) the frequency of the oscillating internal and external cutting edges, and (ii) the dwell time of the internal and external cutting edges when said cutting edges are in the open position while maintaining essentially constant the cutting force exerted by the cutting edges.

2. The surgical instrument as described in claim 1, wherein the cutter drive means comprises an oscillating piston operatively connected to a pneumatic drive system which drives the piston in a forward-rearward manner.

3. The surgical instrument as described in claim 2, wherein the pneumatic drive system provides pulses of gas to the piston forcing the piston to oscillatingly move in a forward-rearward manner.

4. The instrument as described in claim 3, wherein the control means varies the frequency of the pulses as well as the dwell time of the piston in the forward-most position.

5. The surgical instrument as described in claim 1, wherein the instrument includes a piston oscillatingly moveable in a forward-rearward manner, the piston being attached to a barrel cam member having slots therein and cam following pins secured to the internal tube and the external tube, the pins following the slots in the barrel cam member.

6. The surgical instrument as described in claim 1, wherein the cutter is adapted to fit in a surgeon's hand.

7. A method for surgically cutting and removing body tissue from a body joint having restricted space comprising:
   (a) placing a cutter, comprising a body member, an external tube carried by the body member and sized for insertion into the restricted space and having an external opening therein having a cutting edge thereon and an internal tube carried by the body member and positioned within the external tube and having an internal opening therein having a cutting edge thereon, the external and internal openings and cutting edges being relatively oscillatingly moveable to open to receive the body tissue, adjacent the body tissue so that the body tissue is immediately adjacent the external opening;
   (b) drawing the body tissue into the external and internal openings;
   (c) oscillatingly driving both the internal tube and the external tube relative to said body member and in opposite rotational directions with respect to one another causing the internal and external cutting edges to cut the body tissue; and
   (d) independently controlling (i) the frequency of the oscillating internal and external cutting edges, and (ii) the dwell time of the internal and external cutting edges when the cutting edges are in the open position while maintaining essentially constant the cutting force exerted by the cutting edges.

8. The method as described in claim 7, wherein the internal tube is oscillatingly rotated with respect to the external tube.

9. The method as described in claim 7, wherein step (b) is performed by creating a vacuum within the internal tube.

10. The method as described in claim 7, wherein the external tube is stationary and the internal tube oscillates in a forward-rearward manner.

11. The method as described in claim 7, wherein the oscillating frequency of the tubes and the cutting edges is variable.

12. The method as described in claim 7, wherein the dwell time of the cutting edges in the open and closed positions is variable.

13. The method as described in claim 7, wherein step (c) is performed by a piston oscillating in a forward-rearward manner, the piston being secured to a barrel cam member having slots therein and cam following pins secured to the internal and external tubes, the pins following in the slots.

* * * * *